United States Patent
Engleson et al.

(10) Patent No.: US 7,117,041 B2
(45) Date of Patent: *Oct. 3, 2006

(54) SYSTEM AND METHOD FOR PROGRAMMING A CLINICAL DEVICE

(75) Inventors: Joseph J. Engleson, Carlsbad, CA (US); Craig Chamberlain, Ann Arbor, MI (US)

(73) Assignee: Cardinal Health 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/024,564

(22) Filed: Dec. 28, 2004

(65) Prior Publication Data

US 2005/0113945 A1    May 26, 2005

Related U.S. Application Data

(63) Continuation of application No. 10/622,983, filed on Jul. 18, 2003, now Pat. No. 6,915,170, which is a continuation of application No. 09/114,581, filed on Jul. 13, 1998, now Pat. No. 6,671,563, which is a continuation-in-part of application No. 08/440,625, filed on May 15, 1995, now Pat. No. 5,781,442.

(51) Int. Cl.
G05B 19/18 (2006.01)
A61K 9/22 (2006.01)
A61B 5/00 (2006.01)
G05B 15/02 (2006.01)

(52) U.S. Cl. .......................... 700/2; 700/9; 604/890.1; 600/300; 705/3

(58) Field of Classification Search .................. 700/2, 700/9, 17, 214, 232; 604/19, 31; 705/3; 235/275, 380

See application file for complete search history.

(56) References Cited

U.S. PATENT DOCUMENTS

| | | | |
|---|---|---|---|
| 3,848,112 | A | 11/1974 | Weichselbaum et al. |
| 3,898,984 | A | 8/1975 | Mandel et al. |
| 3,921,196 | A | 11/1975 | Patterson |
| 4,164,320 | A | 8/1979 | Irazoqui et al. |
| 4,476,381 | A | 10/1984 | Rubin |
| 4,636,950 | A | 1/1987 | Caswell et al. |
| 4,688,026 | A | 8/1987 | Scribner et al. |
| 4,696,671 | A | 9/1987 | Epstein et al. |
| 4,810,243 | A | 3/1989 | Howson |
| 4,828,545 | A | 5/1989 | Epstein et al. |

(Continued)

FOREIGN PATENT DOCUMENTS

EP    0 595 474 A2    5/1994

(Continued)

*Primary Examiner*—Anthony Knight
*Assistant Examiner*—Ronald Hartman, Jr.
(74) *Attorney, Agent, or Firm*—Fulwider Patton LLP

(57) ABSTRACT

A care management system in which the management of the administration of care for patients is automated. Hospital information systems are monitored and the information from those systems is used in verifying the administrations of care to patients. The care management system monitors ongoing administrations for progress and automatically updates records and provides alarms when necessary. The care management system is modular in nature but is fully integrated among its modules. Particular lists of data, such as the termination times of all ongoing infusions, provide hospital staff current information for increased accuracy and efficiency in planning. Features include the automatic provision of infusion parameters to pumps for accurate and efficient configuration of the pump, and providing an alarm when an unscheduled suspension of an infusion exceeds a predetermined length of time. A passive recognition system for identifying patients and care givers is provided.

14 Claims, 12 Drawing Sheets

U.S. PATENT DOCUMENTS

| | | |
|---|---|---|
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,853,521 A | 8/1989 | Claeys et al. |
| 4,857,713 A | 8/1989 | Brown |
| 4,857,716 A | 8/1989 | Gombrich et al. |
| 4,865,584 A | 9/1989 | Epstein et al. |
| 4,916,441 A | 4/1990 | Gombrich et al. |
| 4,925,444 A | 5/1990 | Orkin et al. |
| 4,978,335 A | 12/1990 | Arthur, III |
| 5,006,699 A | 4/1991 | Felkner et al. |
| 5,036,852 A | 8/1991 | Leishman |
| 5,072,383 A | 12/1991 | Brimm et al. |
| 5,078,683 A | 1/1992 | Sancoff et al. |
| 5,088,981 A | 2/1992 | Howson et al. |
| 5,100,380 A | 3/1992 | Epstein et al. |
| 5,153,416 A | 10/1992 | Neeley |
| 5,153,827 A | 10/1992 | Coutre et al. |
| 5,207,642 A | 5/1993 | Orkin et al. |
| 5,256,157 A | 10/1993 | Samiotes et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,317,506 A | 5/1994 | Coutre et al. |
| 5,367,555 A | 11/1994 | Isoyama |
| 5,374,813 A | 12/1994 | Shipp |
| 5,378,231 A | 1/1995 | Johnson et al. |
| 5,390,238 A | 2/1995 | Kirk et al. |
| 5,401,059 A | 3/1995 | Ferrario |
| 5,416,695 A | 5/1995 | Stutman et al. |
| 5,441,047 A * | 8/1995 | David et al. ............... 600/483 |
| 5,536,084 A | 7/1996 | Curtis et al. |
| 5,547,470 A | 8/1996 | Johnson et al. |
| 5,594,786 A | 1/1997 | Chaco et al. |
| 5,658,250 A | 8/1997 | Blomquist et al. |
| 5,737,539 A | 4/1998 | Edelson |
| 5,738,102 A * | 4/1998 | Lemelson ............... 600/483 |
| 5,781,442 A | 7/1998 | Engleson |
| 5,822,544 A | 10/1998 | Chaco |
| 5,895,371 A | 4/1999 | Levitas |
| 5,912,818 A | 6/1999 | McGrady |
| 5,935,099 A | 8/1999 | Peterson et al. |
| 6,000,828 A | 12/1999 | Leet |
| 6,003,006 A | 12/1999 | Colella |
| 6,021,392 A | 2/2000 | Lester |
| 6,039,251 A | 3/2000 | Holowko et al. |
| 6,053,887 A | 4/2000 | Levitas |
| 2002/0169636 A1 | 11/2002 | Eggers et al. |

FOREIGN PATENT DOCUMENTS

| | | |
|---|---|---|
| GB | 2 141 006 A | 12/1984 |
| WO | WO/95/23378 | 8/1995 |
| WO | WO/96/36923 | 11/1996 |

\* cited by examiner

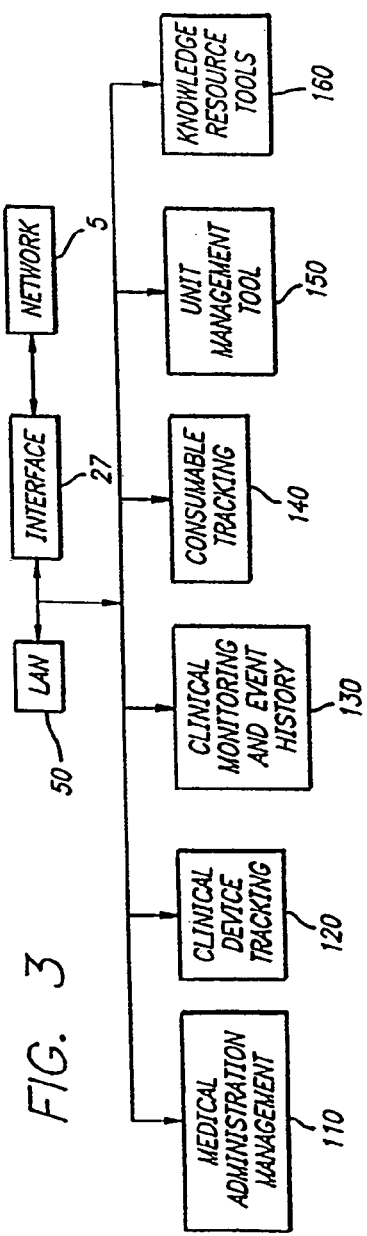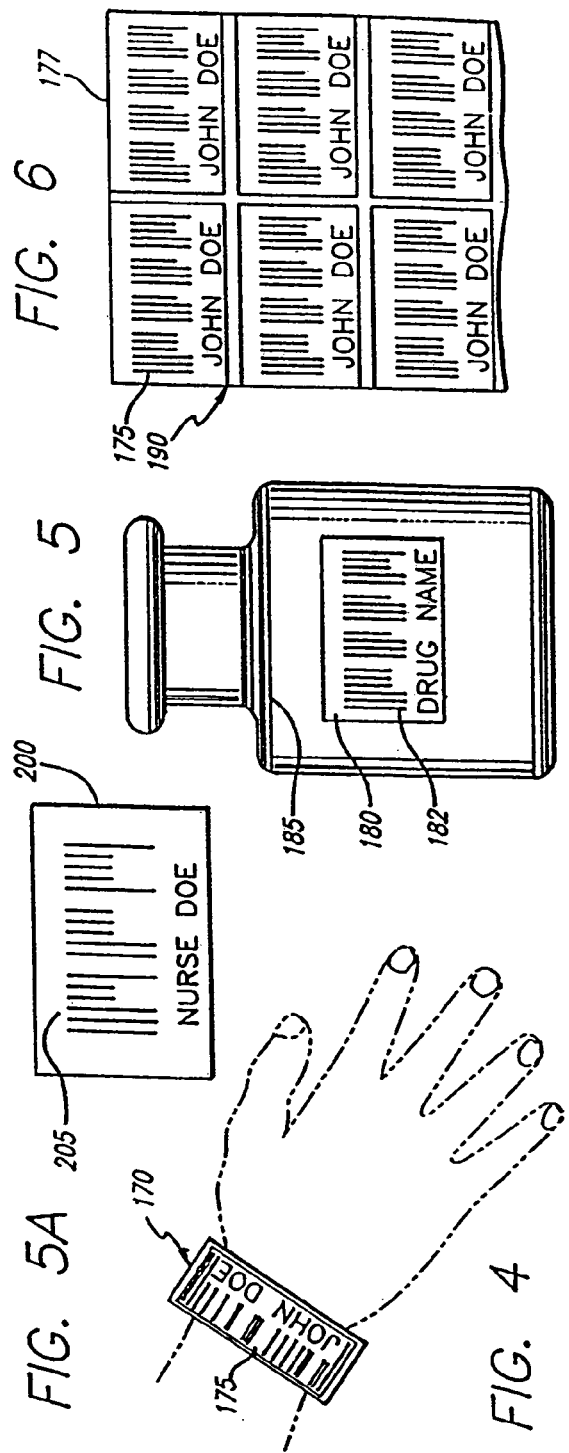

| IVs In Progress | | | |
|---|---|---|---|
| 11 West | | | |
| 25m | DOBUTAMINE | Continuous | 1123 Haaf-Schlemmerstien,* |
| 5h 19m | POTASSIUM PHOSPH* | Continuous | 1123 Haaf-Schlemmerstien,* |
| 7h 25m | MULTIVITAMIN | Continuous | 1139 Ng. Soo Lin Lee |
| 17h 9m | MORPHINE | Continuous | 1136 Dalliance, Mathilda |
| 20h 28m | DEXTROSE 5%-1/2NS* | Continuous | 1125 Van der Wahl, J D |
| 21h 15m | DOPAMINE | PRN | 1136 Dalliance, Mathilda |
| 21h 33m | DOBUTAMINE | Continuous | 1136 Dalliance, Mathilda |

NURSE TASK LIST
04/03/95 1200 – 2359

Reports

| PATIENT | TASK | MEDICATION | NOW 12 | 13 | 14 | 15 | 16 | 17 | 18 | 19 | 20 | 21 | 22 | 23 |
|---|---|---|---|---|---|---|---|---|---|---|---|---|---|---|
| 1123 Haaf–Schlemmerulin, Hans-Fredrich Helmut Wolf 2452116 | | | | | | | | | | | | | | |
| | ADMIN | Cimetidine 300 mg/5 ml Q8H PO | x | | | | | | | | x | | | |
| | NEXT BAG | Dobutamine 250 ml CONTINUOUS IV | x | | | | | | | | | | | |
| | NEXT BAG | Potassium Phosphate 1000 ml CONTINUOUS IV | | | | | | | x | | | | | |
| 1136 Dalliance, Mathilda 2508729 | | | | | | | | | | | | | | |
| | VERIFY | Docusate 1000 ml CONTINUOUS IV | x | | | | | | | | | | | |
| | ADMIN | Nitroglycerine 2 inches Q6H TOP | x | | | | | | x | | | | | |
| | ADMIN | Docusate 100 mg TID PO | | | | | | x | | | | | | |
| | ADMIN | Heparin 100 u/ml Q8H IVP | | | | | | x | | | | | | |
| | ADMIN | Gentamicin 100 ml Q12H IV | | | | | | | | | | x | | |
| 1139 Ng, Soo Un Lee 2517050 | | | | | | | | | | | | | | |
| | ADMIN | Gentamicin 100 ml Q8H IVPB | | x | | | | | | | | x | | |
| | NEXT BAG | Multivitamin 1000 ml CONTINUOUS IV | | | | | | | | x | | | | |

11 WEST

◉ Tasks  ○ Med Summary  ○ Patient Events
○ IVAR   ○ Rescheduled   ○ Alerts  ○ Caregiver

PAGE 1 OF 1

[ Prev ]  [ Next ]  [ Options... ]  [ OK ]

*FIG. 10*

Reschedule Order

Frequency: TID        Order Stop Date/Time: Unspecified

The schedule times for this order are:
0900 1300 1800

Change these times to:
| p900 1300 1800 |

There are no administrations since 05/13/95 0000.

The next administration is scheduled for 05/15/95 0900.
Change this to: | 05/15/1995  09:00 |  ◁  ▷

[OK]   [Cancel]                              [Record Note]

FIG. 11

SYSTEM AND METHOD FOR PROGRAMMING A CLINICAL DEVICE

CROSS REFERENCE TO RELATED APPLICATIONS

This application is a continuation of U.S. Ser. No. 10/622,983 filed Jul. 18, 2003 now U.S. Pat. No. 6,915,170, which is a continuation of application Ser. No. 09/114,581 filed Jul. 13, 1998, now U.S. Pat. No. 6,671,563, issued Dec. 30, 2003, which is a continuation-in-part of U.S. Ser. No. 08/440,625 filed May 15, 1995 now U.S. Pat. No. 5,781,442, issued Jul. 14, 1998.

BACKGROUND OF THE INVENTION

The invention relates generally to systems for managing patient care in a health care facility, and more particularly, to systems for collecting data and controlling the delivery of patient care.

Medical institutions are faced with a competitive environment in which they must constantly maintain or improve profitability and yet simultaneously improve patient care. Several factors contribute to the ever increasing costs of health care, whether it is delivered to the patient in a hospital or out-patient clinic setting. Health care deliverers face increased complexity in the types of treatment and services available, but also must provide these complex treatments and services efficiently, placing a premium on the institution's ability to provide complex treatment while maintaining complete and detailed medical records for each patient.

It is also advantageous to have a care management system that combines all of the various services and units of a health care institution into an interrelated automated system to provide "just-in-time" delivery of therapeutic and other drugs to the patient. Such a system would prevent administering an inappropriate medication to a patient by checking the medication against a database of known allergic reactions and/or side-effects of the drug against the patent's medical history. The interrelated system should also provide doctors, nurses and other care-givers with updated patient information at the bedside, notify the institution's pharmacy when an additional drug is required, or when a scheduled treatment is running behind schedule, and automatically update the institution's accounting database each time a medication or other care is given.

Inaccurate recording of the administration of drugs and usage of supplies involved in a patient's treatment results in decreasing revenues to the institution by failing to fully capture billing opportunities of these actual costs. Inadequate management also results in a failure to provide an accurate report of all costs involved in treating a particular illness.

In many hospitals and clinical laboratories, a bracelet device having a patient's name printed thereon is permanently affixed to a patient upon admittance to the institution in order to identify the patient during his or her entire stay. Despite this safeguard, opportunities arise for patient identification error. For example, when a blood sample is taken from a patient, the blood sample must be identified by manually transcribing the patient's name and other information from the patient's identification bracelet. In transferring the patient's name, a nurse or technician may miscopy the name or may rely on memory or a different data source, rather than actually reading the patient's bracelet.

Moreover, manually transferring other information, such as the parameters for configuring an infusion pump to dispense medication may result in errors that reduce the accuracy and/or effectiveness of drug administration and patient care. This may result in an increased duration of treatment with an attendant increase in costs.

Hospitals and other institutions must continuously strive to provide quality patient care. Medical errors, such as where the wrong patient receives the wrong drug at the wrong time, in the wrong dosage or even where the wrong surgery is performed, are a significant problem for all health care facilities. Many prescription drugs and injections are identified merely by slips of paper on which the patient's name and identification number have been handwritten by a nurse or technician who is to administer the treatment. For a variety of reasons, such as the transfer of patients to different beds and errors in marking the slips of paper, the possibility arises that a patient may be given an incorrect treatment. This results in increased expense for the patient and hospital that could be prevented using an automated system to verify that the patient is receiving the correct care.

Various solutions to these problems have been proposed, such as systems that use bar codes to identify patients and medications, or systems allowing the bedside entry of patient data. While these systems have advanced the art significantly, even more comprehensive systems could prove to be of greater value.

What has been needed, and heretofore unavailable, is an integrated, modular system for tracking and controlling patient care and for integrating the patient care information with other institutional databases to achieve a reliable, efficient, cost-effective delivery of health care to patients. The invention fulfills these needs and others.

SUMMARY OF THE INVENTION

Briefly and in general terms, the present invention provides a new and improved patient management system capable of monitoring, controlling and tracking the administration of care in a health care institution.

Generally, the patient management system comprises a number of CPUs having a variety of input and output devices for receiving patient data and for generating or displaying reports. A system of software programs operates on the CPUs to record, process, and produce reports from a database whose data is representative of the care a patient receives in the institution. The CPUs are connected together, along with at least one dedicated file server, to form a network. Patient data is input by users of the personal computers, and is stored in a data storage device connected to the file server.

More specifically, in a more detailed aspect by way of example and not necessarily of limitation, the patient management system includes a pharmacy computer, a nursing station CPU including a video display and printer and bedside CPUs connected to various clinical devices such as infusion pumps for providing medication to a patient and a barcode reader for reading barcode labels either affixed to the patient's identification bracelet or a label on a medication container. In operation, the patient management system verifies that the right medication is being dispensed to the right patient in the right dosage via the right delivery route at the right time by maintaining a database of information relating to the patient, the patient's condition, and the course of treatment prescribed to treat the patient's illness.

The patient wears an identification device that includes a barcode that can be read by a barcode reader connected to the bedside CPU. Medication to be administered to the patient in the course of the patient's treatment is identified with a label that is printed by a barcode printer in the pharmacy or by the manufacturer's supplied barcodes on unit dose packaging. When the medication is administered to the patient by a care-giver, the care-giver uses the barcode reader connected to the bedside CPU to read the barcode on the patient's identification device and the barcode on the label identifying the medication to be dispensed. The patient management system compares the patient's identity with the medication and verifies that it is the correct medication for the patient. Additionally, the caregiver may also have an identification device that bears a barcode with the caregiver's name and other information. Using the barcode reader, the care giver's identity can thus be stored in the database and linked to the treatment given to the patient to ensure complete and accurate tracking of all treatment given to the patient.

In another aspect, an identification system is provided that is passive in nature. That is, the system operates to automatically detect and identify an individual, such as a patient and/or caregiver without any particular action being required on the part of the individual. In a further aspect, an RF transponder is mounted at a patient's room or treatment area and automatically detects an identification device, such as a wrist band, on the individual to identify the individual. The identification device may comprise an electrical circuit.

In a further aspect, the patient management system also includes the capability of recording the present location of each clinical device in the institution, and maintains a history of the device usage in a device usage and event database. This database may also include a history of a device's maintenance and calibration.

In another aspect, the patient management system includes the ability to track usage of consumable supplies within the various units of the health care institution. This assists in managing the inventory of consumable supplies to ensure that supplies are always available. A further advantage is that it enables the institution's administration to project supply usage and thus purchase supplies in quantities that ensure cost discounts without incurring excessive inventory carrying costs.

In yet another aspect, the patient management system employs RF (radio frequency) transmitters and receivers to connect the various hardware elements of the system together into a local area network. This aspect is advantageous in that it provides increased flexibility in positioning of the hardware elements of the network while eliminating the need for costly network wiring throughout the institution.

These and other advantages of the invention will become apparent from the following more detailed description when taken in conjunction with the accompanying drawings of illustrative embodiments.

BRIEF DESCRIPTION OF THE DRAWINGS

FIG. 3 is a functional block diagram of the software modules that comprise the care system of FIGS. 1 and 2;

FIG. 4 is a graphic representation of a patient identification bracelet including a barcode that can be read by a barcode reader;

FIG. 5 is a drawing of a barcode label affixed to a medication container that can be read by a barcode reader;

FIG. 5A is a drawing showing a barcode label affixed to a caregiver identity badge;

FIG. 6 is a drawing showing a sheet of barcode labels that can be affixed to various containers or devices;

FIG. 8 presents a computer screen listing of the infusions in progress showing the drug being administered, the time remaining, and the patient's name;

FIG. 9 shows a patient IMAR (integrated medication administration record) showing scheduled medications and windows around the scheduled times;

FIG. 10 shows a computer screen task list for a partial floor of a hospital in which times for administration in a certain time period are set out along with the patient name and drug to be administered;

FIG. 11 shows a computer screen used for rescheduling the administration of an order;

DESCRIPTION OF THE PREFERRED EMBODIMENTS

Figure 1:
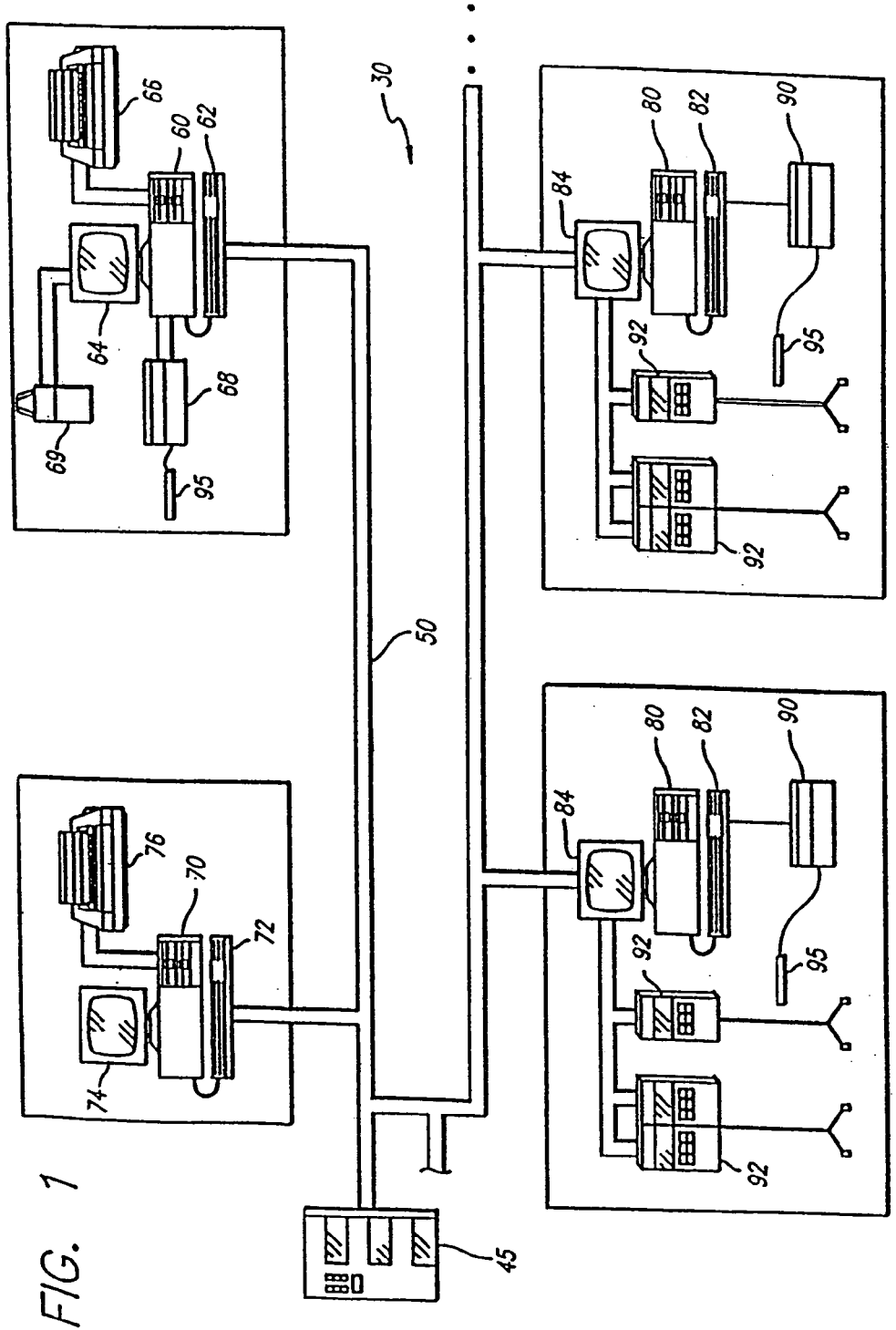
FIG. 1 is a graphic representation of a care management system incorporating principles of the present invention and illustrating details of the hardware elements and local area network.

Referring now to the drawings, and more particularly to FIG. 1, there is shown generally an integrated hospital-wide information and care management system 30 including one embodiment of the point-of-care management system 30 of the present invention. The care management system embodiment shown in FIG. 1 is depicted as being configured as a local area network with a file server 45 to which are connected a pharmacy computer 60, a nursing station 70, and bedside CPUs 80. The file server 45 stores programs and data input and collected by the various computers in the local area network. Various application modules of the patient management system may be resident in each of the computers in the network and will be discussed in more detail below. Ethernet cabling of a local area network 50 is used to connect various CPUs to the file server. The file server 45 also has both local and network hard disk storage for storing programs as well as data gathered on the network.

Figure 2:
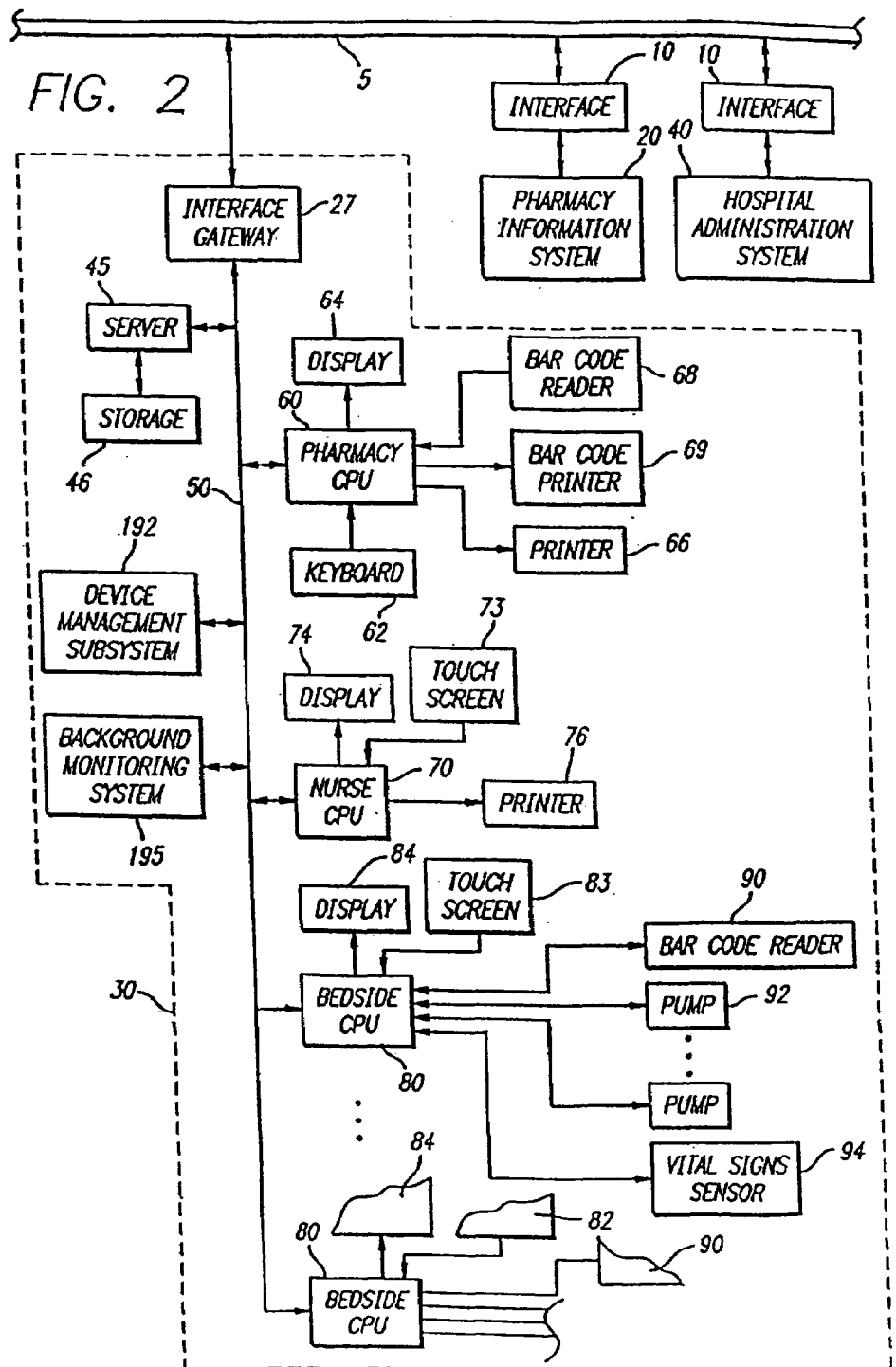
FIG. 2 is a functional block diagram of the care system of FIG. 1 additionally showing an interface with other institutional information management systems.

Referring now to both FIGS. 1 and 2, a functional block diagram of the patient care management system 30 of FIG.

1 is shown in FIG. 2 interfaced with and connected to other hospital information management systems to form an integrated information and care management system. This information and care management system is integrated with a combination of individual hospital systems, such as the pharmacy information system 20, and the hospital administration system 40 which are interconnected via a network 5 and appropriate interfaces 10. Each of the various systems 20, 30 and 40 generally comprise a combination of hardware such as digital computers which may include one or more central processing units, high speed instruction and data storage, on-line mass storage of operating software and short term storage of data, off-line long-term storage of data, such as removable disk drive platters, CD ROMs, or magnetic tape, and a variety of communication ports for connecting to modems, local or wide area networks, such as the network 5, and printers for generating reports. Such systems may also include remote terminals including video displays and keyboards, touch screens, printers and interfaces to a variety of clinical devices. The operating systems and specific software applications will be described in more detail below.

The care management system 30 of FIGS. 1 and 2 includes a file server 45, such as an IBM or IBM compatible personal computer having sufficient mass storage 46, such as local hard drives, CD ROM, magnetic tape, or other media, and appropriate communication interface capabilities to interconnect with other hardware comprising the point of care management system. Although many configurations are possible, in one embodiment the file server would include hardware such as a data communication router, a large hard drive to store data for the entire network, and communication hardware for communicating with the hospital network. Additionally, a separate computer (CPU) is used to communicate with, control and provide an interface gateway 27 to the hospital network 5.

A local area network 50, comprising a thin net, or ethernet cabling is used to connect the central file server 45 to the hardware that comprises the care management system.

In the present embodiment, the file server 45 of the care management system is connected by a local area network (LAN) 50 to computers and other peripheral equipment located in the institution's pharmacy, at nursing stations located throughout the institution, and at the patient's bedside. In the embodiment shown, the module located in the pharmacy comprises a central processing unit 60 to which is attached a video display 64 and a keyboard 62 for entry and display of patient information and drug parameters. Also attached to the pharmacy CPU is a bar code reader 68 which is adapted to read barcode labels that may be attached to drug containers, equipment, or caregiver identification badges as will be more fully discussed below. Also connected to the pharmacy CPU 60 is a bar code printer 69 and a printer 66 used for generating reports containing information about patient history and/or patient treatment. The printer 66 may also be used to print barcode labels generated by the pharmacy CPU 60 after patient or drug data is input by a technician or pharmacist into the pharmacy computer 60 using the keyboard 62 or other means.

Another computer, herein referred to as the nursing CPU 70, is located at a nursing station. Nursing stations are typically located in various sections and/or floors of a hospital or clinic and typically provide a central location for record storage and monitoring for a number of patient beds. The nursing CPU 70 located at the nurse station typically includes a video display 74 for displaying patient or other information pertaining to the operation of the particular unit of the institution, and a keyboard 72, mouse, touch screen 73, or other means for entering patient data or specific commands instructing the nursing CPU 70 to generate reports relating to either the patient's medical history or the course and progress of treatment for an individual patient on the attached printer 76 or on the video display 74. As will be discussed more fully below, the nursing station CPU 70 may also generate other reports such as, for example, a printout of drugs scheduled to be administered to patients, productivity measurements such as, for example, the amount of time a nurse spends with a patient or other reports useful for assisting in the efficient operation of the particular unit or the hospital. For example, a report listing the actual times of administration versus the scheduled times for administration may be prepared to assist in evaluation of staffing requirements.

Each care unit associated with the nursing station typically comprises one of more patient beds located in private rooms, shared rooms, or open or semi-open wards that contain multiple beds. In accordance with an embodiment of the present invention, each private room, semi-private room, or ward area has at least one bedside CPU 80 for monitoring and treating one or more patients. Each bedside CPU 80 has a video display 84 and a keyboard 82, mouse, touch screen 83, or other device. The bedside CPU 80 can be used by a nurse, physician or technician to access a variety of institutional databases to display a variety of information about a particular patient. This information can include an on-line, real-time, graphical patient medication administration record (MAR) that is derived from the patient's medication profile maintained by the hospital's pharmacy information system 20. The bedside CPU 80 also allows remote access to a patient's records stored by the file server 45 to display medication history for the patient. This medication history includes a listing of all drug or other treatments including past, present and future deliveries to the patient. Additionally, access to administration records of the hospital's administration system 40 is available through the network 5.

Each bedside CPU 80 can be connected through an appropriate interface to a variety of peripheral equipment. For example, a barcode reader 90 capable of reading barcodes on a patient's wristband or medication container; an infusion pump 92 for delivering medication to the patient in a predetermined, controlled manner; or various sensors 94 that can automatically monitor a patient's vital signs and send signals representative of these vital signs to the computer through an appropriate interface for storage and later retrieval by a selected software application to provide a graphic display of the patient's vital signs during the course of treatment.

A plurality of bedside CPUs are shown in the drawing; however, more or fewer may exist depending on the particular system and hospital requirements.

Referring now to FIG. 3, a block diagram illustrating the various application software modules comprising the care management system 30 is shown. The care management system's 30 application software is modular in construction to allow installation and operation of the system with only one or more of the application software groups present. This provides flexibility in meeting the widely varying needs of individual institutions where cost and complexity may be an issue or where the full system is not needed. Each of the modular applications, however, is fully integrable into the system.

The programs of the care management system 30 control alarms or alerts generated by one of the modular applications. Alarms are routed automatically to the appropriate video display. For example, an occlusion alarm generated by a pump 92 may remain local for a predetermined period. After that period the patient's bedside computer 80 may then broadcast the alarm by causing the alarm to be communicated over the LAN 50 to alert other hospital staff of a potential problem or to cause a particular person responsible for the care of a patient, such as, for example, a physician or nurse, to be paged.

Each of the modular applications will now be described in detail. The operation of each of these modular applications in a clinical setting will be discussed more fully below. The medical administration management module 110 integrates medical order information, infusion pump monitoring, and barcode technology to support the real-time verification and charting of medications being administered to a patient. The medical administration management module 110 creates and maintains an on-line, real-time, patient-specific medication administration record ("MAR") or integrated medication administration record ("IMAR") for each patient. This medication administration module 110 contains all of the information generated in the institution regarding the care provided to the patient. The medication administration management module 110 gathers information from the various nursing and bedside CPU's 70, 80 (FIG. 1) comprising the peripheral hardware of the care management system 30 that is distributed throughout the institution. For example, when a physician attending a patient diagnoses an illness and determines an appropriate course of treatment for the patient, the physician may prepare a handwritten medical order specifying the desired therapeutic treatment as well as any appropriate parameters such as dosage and/or period of administration. The written prescription is sent through the institutional mail system to the pharmacy where it is then entered into the pharmacy information system 20 through a dedicated terminal, or other means, and is then entered into the care management system 30.

In another embodiment, the physician accesses the pharmacy management system 20 through a dedicated terminal or through the care management system 30 via the network 5 using either a nursing CPU 70 or a bedside CPU 80. Alternatively, the treatment order may be entered by a nurse or other qualified caregiver into either the pharmacy management system 20 or the care management system 30.

Referring now to FIGS. 4–6, a variety of implementations of the barcode identification system of the present invention are shown. FIG. 4, for example, shows a patient identification bracelet 170 of the kind typically used in hospitals and other institutional settings to ensure that each patient is able to be identified even if the patient is unconscious or otherwise unable to respond to questioning. A barcode 175 is printed on a label that is attached to the patient identification bracelet 170 and has encoded within its sequence of bars the information necessary to identify the patient. This barcode may be read using a computerized barcode reader 68, 90, such as those shown connected to the pharmacy CPU 60 and the bedside CPUs 80 (FIG. 1). The barcode reader comprise a light emitting and receiving wand 95 that is scanned across the barcode. The light emitted by the wand 95 is reflected by the sequence of dark and light lines comprising the barcode into the receiving lens of the wand 95. A sensor in the wand 95 converts the received light into a signal that is then transmitted to the CPU. A software application program running on the CPU then decodes the signal into the data represented by the barcode in a manner well known to one skilled in the art. Using appropriate software programs, this data may then be automatically entered into a database stored in the CPU's memory or disk storage. While a barcode has been described for purposes of illustration, those skilled in the art will immediately understand that other systems, such as magnetic stripes, or programmed punched holes may also be used to represent data stored on each label, care giver badge or patient wrist band.

Barcode systems are extremely flexible and the amount of information that can be represented by the barcode, while limited, can be used in a variety of ways. For example, as depicted in FIG. 5, a drug container 185 is identified by a label 180 having a barcode 182 printed thereon. This barcode 182 can represent the patient identification and the medical order number, and any other information the institution finds helpful in dispensing the drug and tracking the treatment. The barcode 182 may also be read using a barcode reader, and, using suitable application software such as that included within the medical administration management module 110, discussed below, can be used to link the drug container and its contents with the patient identification bracelet 170 affixed to a patient to ensure the right drug is delivered to the right patient at the right time in the right manner. The use of barcodes is not limited to the implementations discussed above. A sheet 190 of barcode labels 177 having barcodes 175 is shown in FIG. 6. Such labels can be printed by a printer connected to the pharmacy CPU 60 of the care management system 30 or, alternatively, by any other printer connected to any other hospital information system that can be programmed to produce barcodes bearing the information in a form that can be read by the barcode readers connected to the various CPUs of the care management system 30. These barcode labels 177 may then be affixed to clinical devices, patient belongings, or other items where positive identification is needed.

One of the key advantages of the medical administration management module 110 (FIG. 3) is that the module works in concert with the barcode labels described above. When the medication administration management module 110 is implemented using the hardware system described above comprising a pharmacy CPU 60, barcode reader 68, and printer 66, together with a bedside CPU 80 with a connected barcode reader 90, the care management system 30 ensures that medication is administered to the right patient, in the right dose, along the right route and at the right time.

Figure 7:
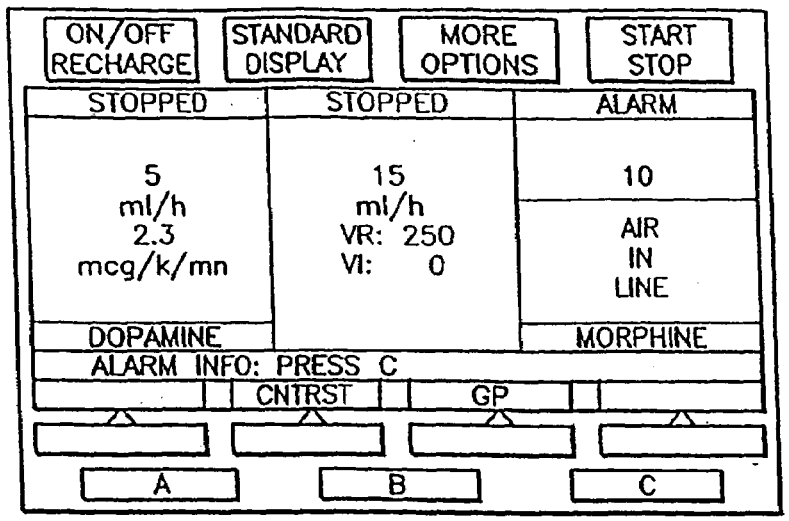
FIG. 7 is a graphical representation of a display on an infusion pump showing the name of a drug being infused along with other information relating to the infusion.

When the medication to be administered is of the type that is typically delivered to the patient using an infusion pump, the medical administration management module 110 automatically records the start time of the infusion, queries the pump periodically throughout the infusion and maintaining a continuous log of the infusion, and records the end time of the infusion and the volume infused in a patient's MAR. If the infusion pump connected to the bedside CPU has a programmable display, the name of the drug, as well as other important information concerning the progress of the infusion can be displayed on the infusion pump throughout the infusion to provide a visual display of the status for the infusion. One such pump is shown in FIG. 7. The particular infusion pump depicted in FIG. 8 has three pumping channels. Two of the channels are displaying the name of the drug being infused.

Because the medication administration management module 110 maintains an on-line, real-time, patient specific graphical medication administration record that includes both past, present and future scheduled medications, a nurse may select a scheduled dosage on the MAR and indicate that it will not be administered for specified reasons selected from a list of options that are dependant upon the health status of the patient at a particular time. This system also allows a nurse to select a scheduled dose on the MAR, and record notes and observations about the dose selected from a list of options. The medical administration management module 110 also provides on-line, real-time help screens that can be accessed by a nurse or other caregiver to display specific information about selected medication and dose to be dispensed.

The medication administration management module 110 provides a list of on-going infusions that can be displayed on the video display of the pharmacy CPU 60 such as is shown in FIG. 8. Drug administrations that will terminate within a preselected time period may be distinguished from other administrations by color highlighting or other means. The time remaining, drug, and patient name are presented as well as buttons for program control.

The medication administration module 110 records and maintains in a stored file a log of alerts that are generated when any discrepancy is identified, for example, during the verification process which will be discussed more fully below. The medication administration module 110 also allows the nurse to acknowledge and correct the discrepancy in real-time, or override the alert by entering the appropriate command. Even where the nurse is allowed to override the alert, the medication administration application module 110 prompts the nurse for a reason for each alert override and then automatically enters the reason into the MAR for the patient.

Figure 9:
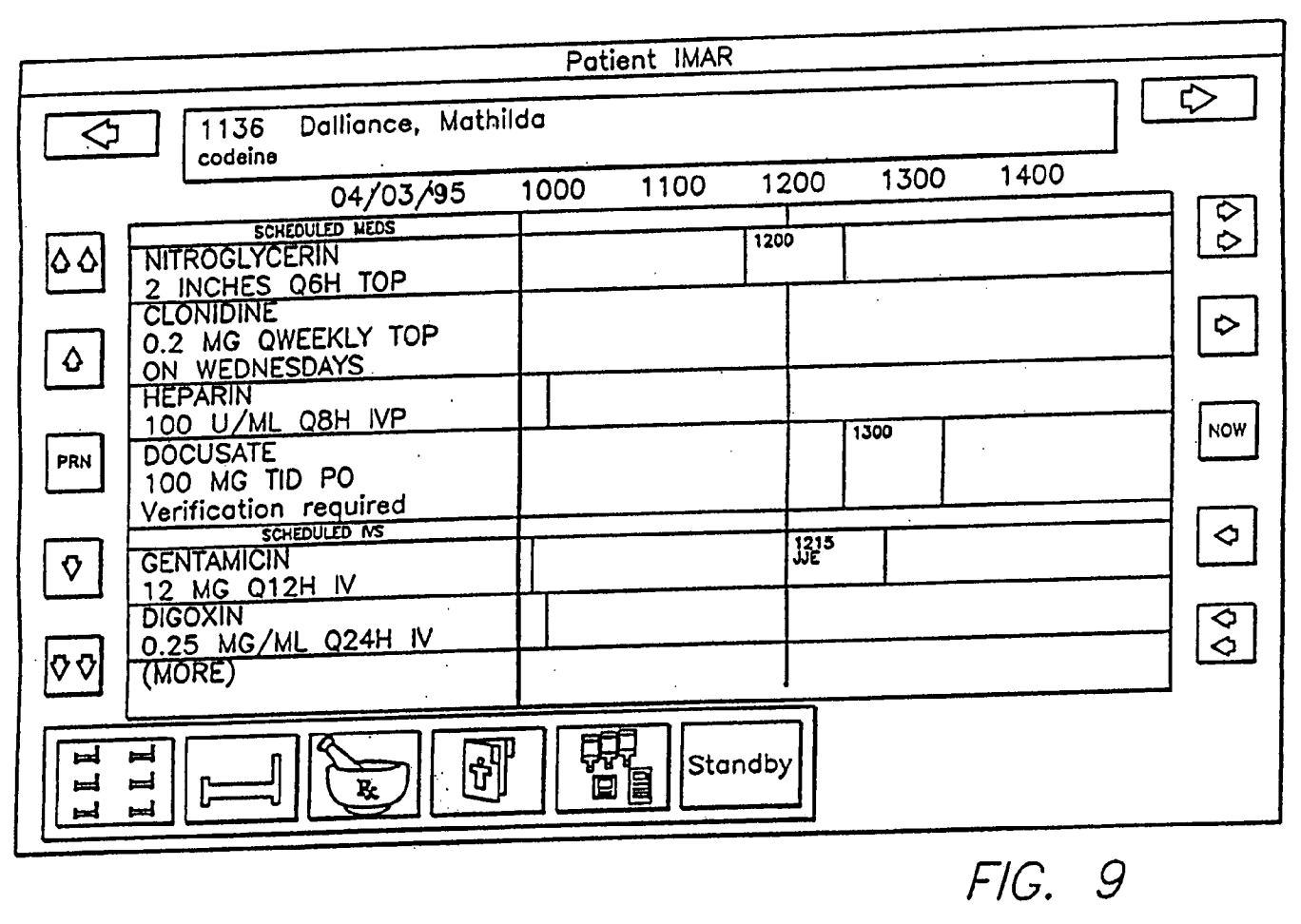

The medication administration management module 110 assists the nurse or other health care professional in efficiently delivering care to the patients by providing the ability to perform on-line queries of the patient's MARs and produce reports designed to assist the nurse in planning medication administration and in scheduling the workload of dispensing the medication to the many patients for which a nursing unit is typically responsible. For example, the video display may be color coded to indicate the status and schedule of each drug administration, such as the patient's IMAR shown in FIG. 9. A drug delivery window extending from thirty minutes prior and thirty minutes after the scheduled administration time may be indicated by a yellow band on the display. Other reports such as the FIG. 10 task list may, for example, include scheduling of drug administrations to ensure proper medication of the patient while distributing the workload over a period of time to ensure that all medication is given promptly. The system may also display either visuals alerts on the nurse station video display 74 or produce a printed report on the printer 76 to provide a permanent record of any medication administration that is running late or has been rescheduled. The medication administration module 110 may be programmed to operate in an automatic fashion, automatically providing standard reports at the nursing station at predetermined intervals, such as, for example, every 30 minutes, as determined by the needs of the particular nursing unit and institution.

The clinical monitoring and event history module 130 shown in FIG. 3 is designed to monitor a variety of clinical devices attached to the network in a real-time manner and provides information about those devices to monitoring stations located elsewhere on the network. For example, the clinical monitoring and event history module 130 can be configured to monitor a plurality of clinical devices that are in use to deliver medication to patients in the private rooms, semi-private rooms or ward areas in a nursing unit. The clinical monitoring and event history module 130 retrieves real-time data from each device, and displays a visual representation of each device including all significant data related to its status and settings on the video display 74 connected to the Nursing CPU 70 (FIGS. 1 and 2). For example, in the case where the clinical monitoring and event history module 130 is monitoring an infusion pump 92, a nurse at the nursing station can access the status for that pump wherein the display 74 attached to the nurse CPU 70 then displays information regarding the status of the infusion being performed at that time. For example, information can include the name of the drug being infused, the patient's name, the scheduled start, the actual start of infusion, the scheduled end of infusion, the projected end of infusion, the amount of drug infused, the amount of drug remaining to be infused and any alert or discrepancy conditions that may need attention by the nurse. Because the care management system 30 is a fully integrated system, the medical administration management module 110 works in concert with the clinical monitoring and event history module 130 so that a nurse, doctor or technician may, after evaluating the status of the infusion displayed on either the video display 74 at the nursing CPU 70 or on the video display 84 at the bedside CPU 80 may, by using the touch screen 73, 83 of the computer, adjust the infusion regimen accordingly using, for example, a screen displayed on the video display 74, 84 as shown in FIG. 11.

Figure 12:
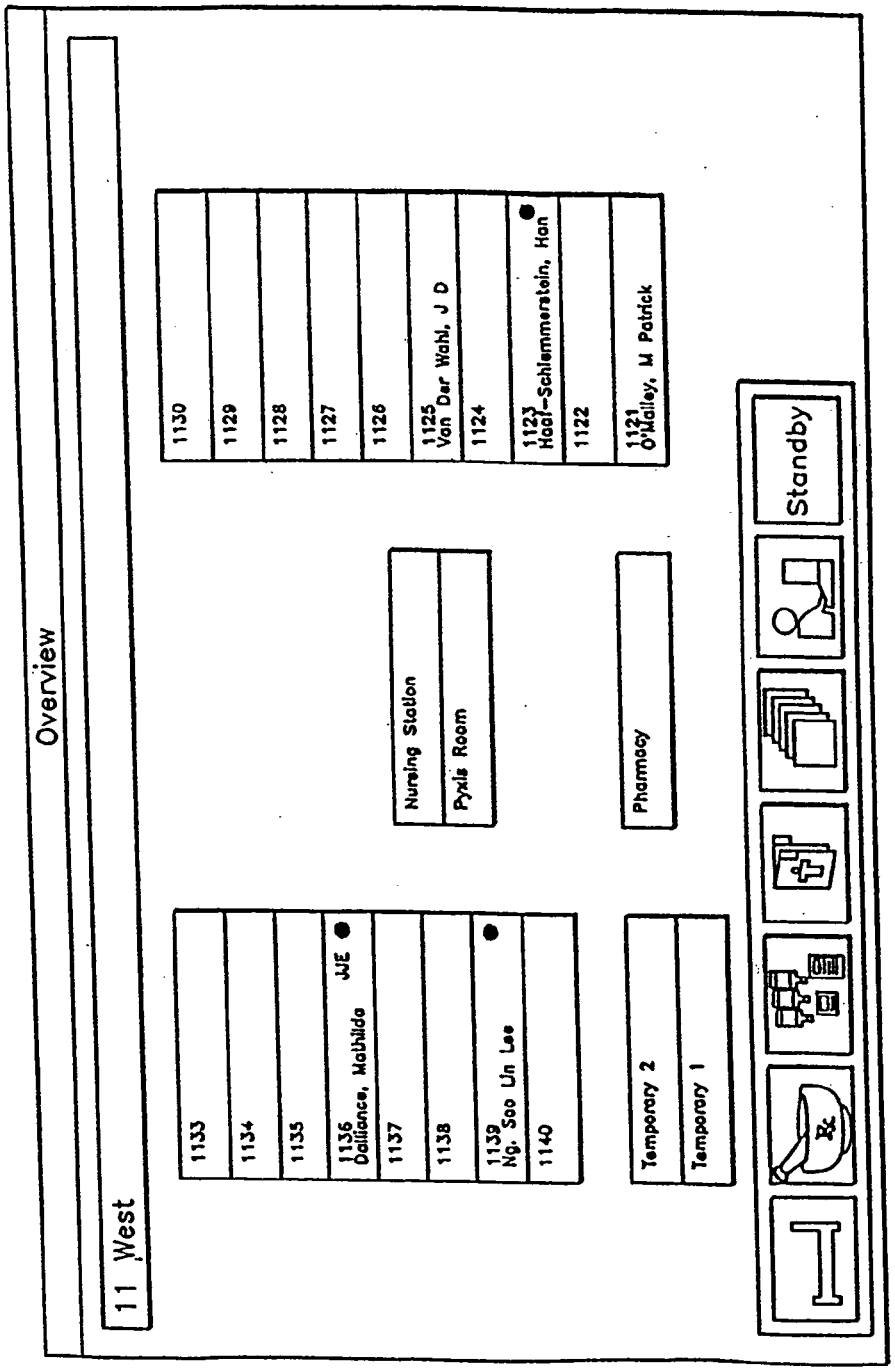
FIG. 12 presents a computer screen containing an overview of a partial floor of a hospital in which various patients' rooms are shown with the names of the patient.

The clinical monitoring event history module 130 may also be programmed to immediately display alarm conditions on remote monitoring screens, such as the video display 74 attached to the nursing CPU 70, as the alarm occurs. For example, the status of each patient's infusion can be represented on a video display at the nursing station as shown by the OVERVIEW computer screen in FIG. 12. When an alert occurs, the box representing the patient' room flashes red to attract attention to the alert. Displaying the alarm condition in this manner allows a nurse to quickly and easily identify the patient from the nursing station and take appropriate action to address the condition causing the alarm. The system may also be programmed to display certain alarms that have been identified as particularly important events at other video displays located throughout the institution, such as the video display 64 attached to the pharmacy CPU 60 located in the institution's pharmacy. The manner of overview display in FIG. 12 also facilitates record update. For example, when patients move rooms, clicking on the patient's name, dragging that patient to the new room, and unclicking will cause the records to reflect the patient's move and the display will now show the patient in that room.

The clinical device tracking and reporting module 120 shown in FIG. 3 is used to maintain a record of the location of each clinical device and the history of its use in the institution. This system maintains a record of the current or last known location within the institution of each clinical device used in the institution, such as an infusion pump or vital sign sensor. Thus, the appropriate equipment can be easily located by a nurse or a technician for a given therapy regimen or vital sign measurement. This is particularly useful in a large hospital or clinic having many patient rooms, patient beds, or treatment areas where equipment may be temporarily misplaced. This system is also useful in those particular instances where an emergency occurs where treatment requires a particular piece of equipment. The status of that equipment can be easily ascertained from a remote video terminal, such as the video display 74 connected to the nursing CPU 70.

The clinical device tracking and reporting module 120 also maintains a record containing the usage history of each clinical device, including information about the patient it was used to treat, its location, the date, time, duration of use, any alarms that occurred and what medications were dispensed. This history may also contain the maintenance and calibration records for a clinical device. Such information can be queried on-line by technicians, nurses or other hospital administration personnel to generate reports to assist in locating the clinical device, report on the historical usage of the device, and to provide a log of preventative maintenance and equipment calibration. The efficient calibration of complex and sensitive clinical devices is particularly important in a heath care institution to maintain accuracy and quality of therapeutic treatment delivery. Maintaining a history of the usage of the device is also helpful to justify purchasing additional clinical devices when needed, or where the record indicates that a particular clinical device has become obsolete and needs to be replaced by a newer model of the device.

The care management system 30 also includes a consumable tracking module 140 that maintains a record of all consumable item usage for treatment of each patient. This record ensures that appropriate supplies are ordered and delivered to the nursing unit in a timely and cost-efficient manner to prevent outages of necessary supplies. Such information may also be used by the hospital inventory systems through an appropriate interface or other management system to ensure that the supply purchasing is done as cost-effectively as possible. The consumable tracking module 140 provides on-line queries and report generation summarizing consumable uses for a particular patient, a particular nursing unit, or a variety of other purposes.

The unit management tool module 150 assists nurses in sharing information related to patients and automates routine transactions within the nursing unit. The unit management tool module 150 allows a nurse to record the allergies, handicaps, and special care needs of the patient which, cooperating with the medication administration record module 110 and the clinical monitoring and event history module 130, displays that information prominently on all appropriate display screens, either at the pharmacy video display 64, the nursing video display 74 or at the bedside video display 84 (FIG. 1). The unit management tools module 150 also allows a nurse to record patient transfers and the times when the patient is out of the room or off the floor, such as, for example, when the patient is transferred to surgery or to a different part of the institution for a particular kind of treatment such as rehabilitative therapy. This system may also be programmed to signal an alarm when a patient has been disconnected from the system longer than scheduled, for example, when the patient disconnects from the infusion to attend to personal hygiene. This function ensures that an alarm or alert is sounded and that appropriate personnel are notified of any potential problems and can take the necessary actions to alleviate the alert condition.

The knowledge resource tools module 160 provides a framework for information sharing among the various units in the hospital and also supports an assortment of everyday tools to used by the nurses, physicians and technicians involved in the delivery of health care within the institution. This module allows or assists in integrating external information sources into the care system 30 to improve the effectiveness of the care management team in treating the patients in the institution.

For example, the knowledge resource tools module 160 provides a variety of on-line tools including, for example, a calculator, a dose rate calculator for calculating the appropriate dosage and infusion rate for a particular drug to be infused into a patient, a standard measurement conversion calculator for converting between units of measurement, a skin surface area calculator, and a timer and stopwatch. These resources may be displayed on the video displays 64, 74, 84 at appropriate points within the system, and are available from any CPU either in the pharmacy, at the nursing station or at the bedside. These application tools can be programmed to appear on the video display 64, 74, 84 either automatically, such as, for example, when an infusion pump is configured at the start of an infusion to assist in the calculation of a dose rate. These resources may also be available upon entry of the appropriate command by a nurse, physician or technician.

Referring once again to FIG. 2, a device management subsystem 192 is shown and comprises a microcomputer. The subsystem monitors the status of the clinical devices, such as the pumps. Alternately, the subsystem 192 may be included in another microcomputer, such as a bedside CPU 80.

The background monitoring system 195 may also be disposed in a stand-alone microcomputer or may be incorporated in an existing microcomputer. The subsystem performs background tasks such as monitoring the status of the interface gateway 27.

As depicted in FIG. 2, the care management system 30 is connected to other systems in the institution via an interface 10. This interface may support standard health level 7 (HL7) interfaces to the hospital's other information systems and can also support custom interfaces to systems or devices that do not support the HL7 standard. The system interfaces may be either real-time or batch mode, although a real-time interface to a hospital's pharmacy system is required to support the on-line medical administration records keeping function of the medical administration management module 110.

The care management system software can be written to operate on a variety of operating systems to suit the needs of a variety of institutions. In a present embodiment, the software is written to interface with the nurses and physicians using the Windows environment (Windows is a trademark of Microsoft, Inc.) on IBM compatible micro-computers. The Windows environment is well-known by those skilled in the art and will not be described in detail herein. The care management system software, when implemented using the Windows system, is particularly useful in that the Windows operating system provides the ability to load several programs at once. Multitasking programs, allowing several application programs to run simultaneously yet providing immediate access to the various software modules of the care management system 30 may also be used.

One particular mode of operation of the care management system will now be described. As described above, a patient entering a hospital or other care-giving institution is provided with a wristband necklace, ankle band or other identifier that is affixed to the patient in a manner so that the patient can be identified even if the patient is unconscious or otherwise unresponsive. Such a wristband 170 is depicted in FIG. 4. In one embodiment, the wristband 170 barcode represents the name of the patient and other information that the institute has determined is important and also includes a barcode 175. The information printed upon the band, such as name, age, allergies or other vital information is encoded into the barcode 175.

After the patient is admitted and situated in a bed within the institution, the patient is typically evaluated by a physician and a course of treatment is prescribed. The physician prescribes the course of treatment by preparing an order, which may request a series of laboratory tests or administration of a particular medication to the patient. The physician typically prepares the order by filling in a form or writing the order on a slip of paper to be entered into the hospital's system for providing care.

If the order is for administration of a particular medication regimen, the order will be transmitted to the institution's pharmacy. The order will arrive in written form at the pharmacy, will be evaluated by the pharmacy and processed. The pharmacy then prepares the medication according to the requirements of the physician. The pharmacy packages the medication in a container, such as the container 185 shown in FIG. 5. Normally, a copy of the order, or at a minimum, the patient's name, the drug name, and the appropriate treatment parameters are represented on a label that is then affixed to the drug container 185. According to one embodiment of the present invention, this information is represented by a barcode 182, that is then printed on a label 180. This barcode label 182 may be automatically generated using a printer capable of printing barcodes, such as, for example, a printer 69 attached to the hospital's pharmacy information system 20. The existence of this medication order is made available by the hospital's pharmacy information system 20 and is stored by the file server 45.

Generally, the medication is then delivered to the appropriate caregiving unit for administering to the patient. A nurse or technician carries the drug container 185 to the appropriate patient. In accordance with one embodiment of the present invention, the nurse or technician first read the barcode 175 on the patient ID bracelet 170 using the barcode reader 90 connected to the bedside CPU 80. The nurse or technician would then read the barcode 182 on the label 180 affixed to the drug container by swiping the barcode wand 95 across the barcode 182 printed on the label 180 of the drug container 185. Additionally, a record of the identity of the caregiver dispensing the medication may be obtained by reading the barcode 205 printed on an identity badge 200 (FIG. 5A) typically worn by all institution personnel.

For certain drugs, the care-giver is prompted to enter data descriptive of a selected patient parameter or parameters, such a laboratory value or a current vital sign, before completing the verification process. For example, the caregiver may be prompted to measure and enter a value for a patient's blood pressure before administering certain selected drugs. The system may include ranges of acceptable values for the parameters. If the system detects an out-of-range value for the parameter, the system causes an alarm to be provided. In an alternative embodiment, the parameters could be monitored and entered into the system automatically, eliminating the need for manual entry by the caregiver.

The data obtained then is analyzed by the medication administration management module 110 which records the therapeutic regimen information in the patient's MAR, and verifies that the right medication is being given to the right patient in the right dose by the right route and at the right time. If the medication administration management module 110 detects a discrepancy between the barcoded information printed on the patient bracelet 170 and the barcoded information on the label 180 affixed to the medication container 185, an alert is sounded and the appropriate information is displayed on the video display 84 attached to the bedside CPU 80. The nurse or technician then either corrects the discrepancy by either re-reading the barcode 175 on the patient's bracelet 170 and the barcode 182 on the medication container 185 or, alternatively, by entering the appropriate information into the bedside CPU 80 using the keyboard 82 or touch screen 83, mouse, or other device. In the event that the nurse or technician determines that the discrepancy cannot be automatically corrected by re-reading the barcodes and that the discrepancy is minor and will not affect the accuracy or safety of the delivery of the medication, the nurse or technician may override the alert.

In an embodiment of the present invention, where the medication is to be delivered using an infusion pump, such as the infusion pumps 92 attached to the bedside CPU 80, the care management system automatically downloads information consisting of the appropriate configuration parameters for the infusion from the pharmacy CPU 60 through the local area network 50 into the bedside CPU 80 and then into the infusion pump 92 when the verification function of the medical administration management module 110 is complete. This is particularly advantageous in that one potential source of inaccuracy is eliminated by automatically configuring the pump, thus eliminating the need for the nurse or technician to manually enter the parameters necessary to configure the infusion pump 92. In one embodiment, the infusion pumps 92 comprise IVAC Corporation Model 570 volumetric pumps. In an embodiment where the pumps cannot be automatically configured by downloading parameters from the network, the care management system 30 only verifies that the right treatment is being administered to the right patient. The pump must then be manually configured by the physician, nurse or technician.

Once the infusion pump is configured, the technician then starts the infusion by pressing the appropriate control on the infusion pump 92. Starting pump that is capable of being monitored automatically by the care management system 30 causes a signal to be transmitted from the pump to the bedside CPU 80 which is then logged by the clinical monitoring and event history module 130 and entered by the medical administration management module 110 into the patient's MAR. In the case where the institution is using a pump that is not capable of being configured by downloading parameters from the network, the nurse or other caregiver logs the start of the infusion using the touch screen device, mouse or other device connected to the bedside CPU 80. In this case, the video displays of the care management system 30 that display information about the status of the infusion will not display real-time data. Rather, the care management system 30 will project what the status of the infusion should be given the infusion parameters, the time elapsed since the infusion began, and any other events that were manually logged by the caregiver that may have affected the progress of the infusion.

The care management system 30, utilizing the application modules described above, monitors the infusion process in a real-time manner, providing alerts on the appropriate video display screens located throughout the institution and allows intervention by nurses or other caregivers at remote locations if necessary. If the pharmacy management system 20 is directly linked to the care management system 30, the care management system 30 may also provide a scheduling report to the pharmacy in determining the status of ongoing infusions, as well as in scheduling the preparing of medications for future infusions.

In another embodiment, the present invention includes a "Code Mode" that allows a care-giver to bypass the system to immediately cause a list of drugs that have been preselected by the institution to be used in an emergency situation. The initiation of the "Code Mode" causes a time-stamp to be placed in the patient's MAR along with the identity of the drug selected from the displayed list of drugs to be used to treat the emergency. This feature ensures that the emergency, and the treatment used to address the emergency, are accurately recorded in the patient's MAR.

Figure 13:
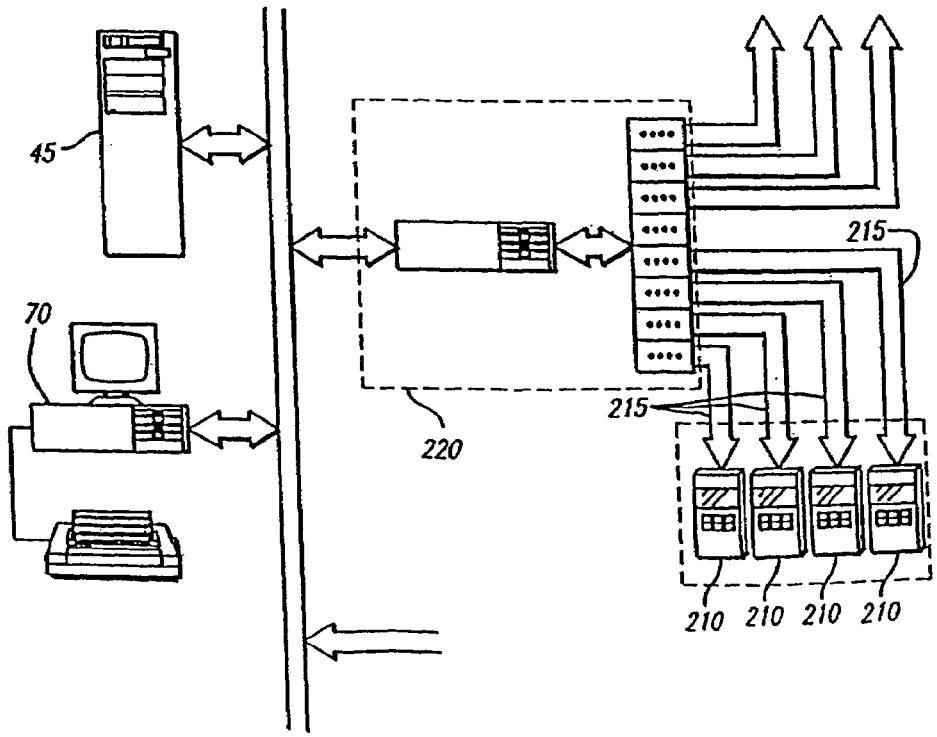
FIG. 13 is a graphical representation of another embodiment of the care management system showing the clinical devices connected to the local area network through a bedside data concentrator.

While one particular embodiment of the present invention has been described above, alternative configurations of the care management system network are possible. For example, one alternative embodiment of the care management system 30 is depicted in FIG. 13. In this configuration, clinical devices 210 are connected by means of appropriate interfaces and cabling 215 to a bedside data concentrator 220 which would typically be located outside of a private room, semi-private room or ward area. In this configuration, there is no bedside CPU 80 as described previously. Instead, the bedside data concentrator 220 is connected through an appropriate interface and cabling to the local area network 50, where the data gathered from the clinical devices 210 is then available for processing by the care management system 30 and display at the various monitoring stations, such as either in the pharmacy or at the nurse station 70. In this embodiment, there is no bedside CPU 80 having a keyboard 82 for data entry or a video display 84 for display of either clinical device information or patient information.

Figure 14:
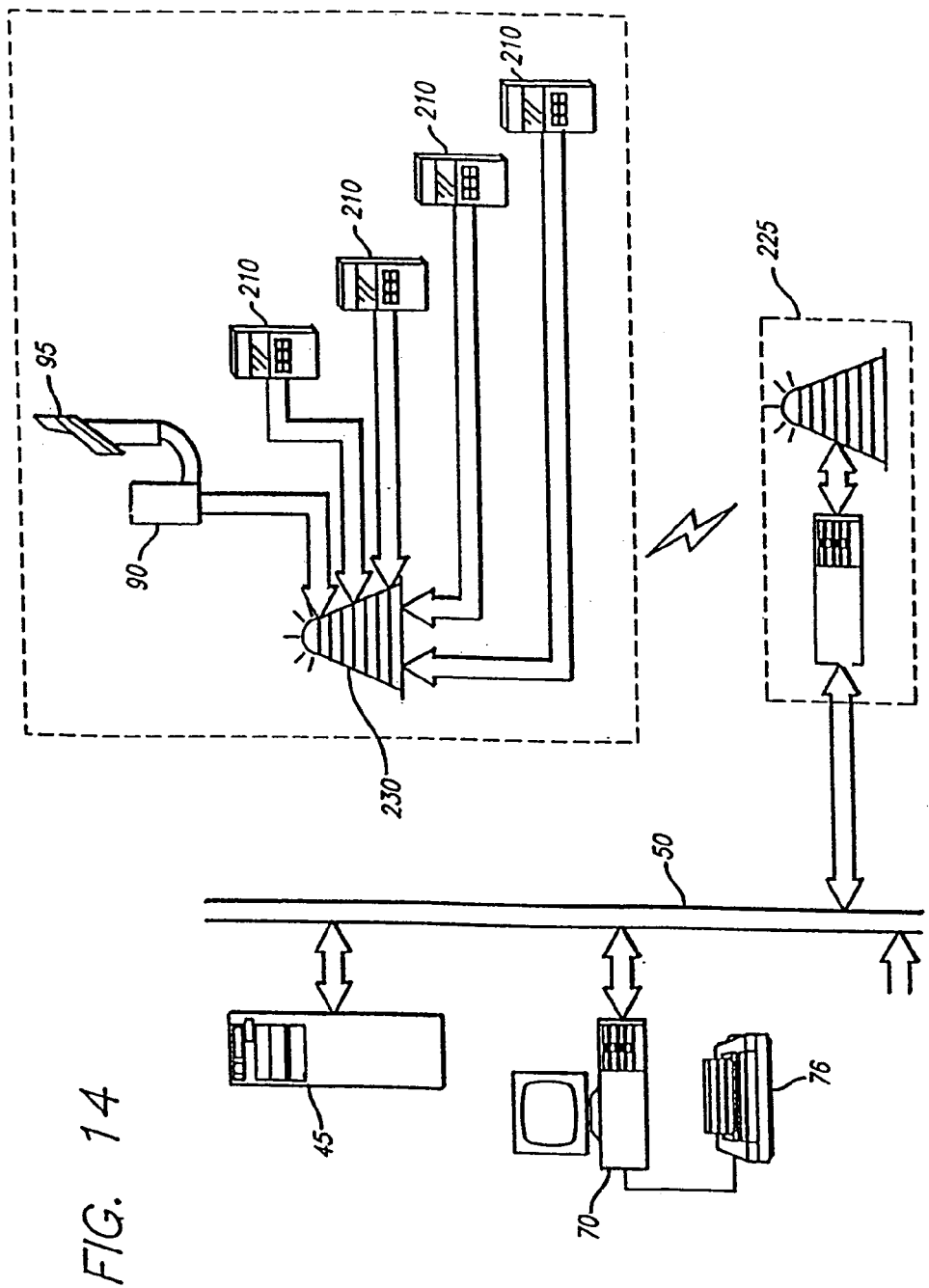
FIG. 14 is a graphical representation of still another embodiment of the care management system showing the clinical devices transmitting and receiving information from the local area network through RF transmitting/receiving equipment.

A further embodiment of the care management system 30 local area network is depicted in FIG. 14. In this embodiment, the file server and monitoring stations are connected using appropriate interfaces and ethernet cabling to an RF data concentrator 225. At the bedside locations in the private rooms, semi-private rooms or ward areas of the institution, the clinical devices 210 and barcode reader 90 at the bedside are connected to an RF transmitter/receiver 230. This RF transmitter/receiver 230 transmits the information gathered from the clinical devices 210 and the barcode reader 90 to the RF data concentrator 225 attached to the local area network 50. Thus, expensive cabling is not required to connect every patient treatment area. Additionally, flexibility in locating the clinical devices 210 and barcode reader 90 is obtained as well as allowing the ability to reconfigure the patient treatment area without costly rewiring of the ethernet cabling.

Figure 15:
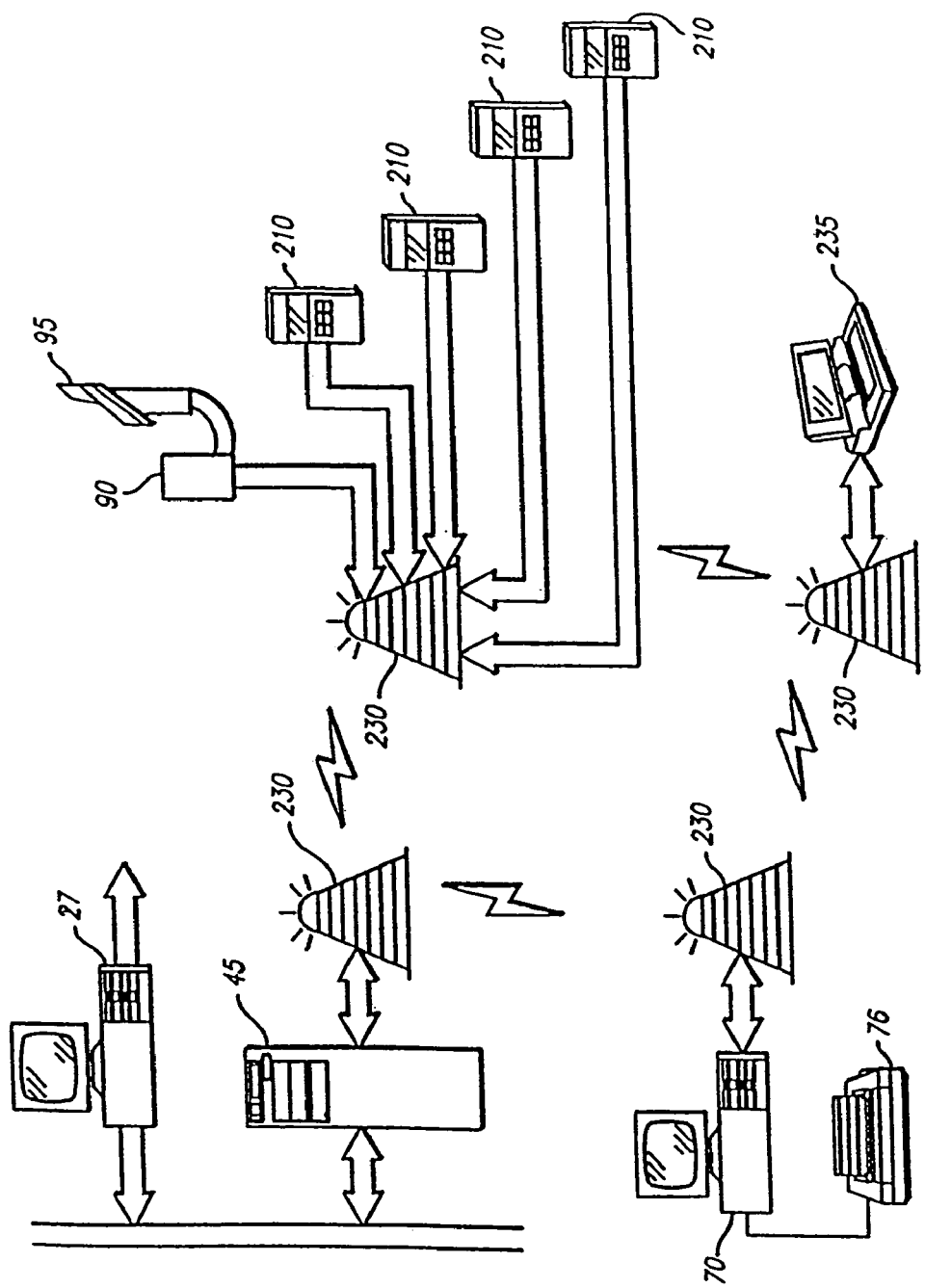
FIG. 15 is a graphical representation of another embodiment of the care management system of FIG. 9 where all of the hardware elements of the local area network communicate with each other using RF transmitting/receiving equipment.

Yet another embodiment of the care management system 30 local area network 50 configuration is shown in FIG. 15. In this configuration, the ethernet cabling connecting the pharmacy CPU, the nurse station nursing CPU 70 and bedside. CPUs and clinical devices is eliminated entirely. Each hardware element, comprising the file server, nursing CPU 70, pharmacy CPU 60 and bedside CPUs 80 and clinical devices and/or barcode readers is connected to an RF transmitter/receiver 230. In this manner, all of the information is transmitted throughout the local area network 50 by way of radio transmission rather than by using costly network cabling. Such a system would additionally allow for the use of portable computers 235 having RF transmitter/receivers 230 that could then be carried with physicians, nurses or technicians as they circulate through the institution. With this configuration, caregiving personnel could access the care management system either spontaneously or upon notification of an alert no matter where they were in the institution at any given time. Such a system would be particularly useful in a large institution where caregiving personnel are likely to be responsible for many hospital beds or when personnel are out of the area or off the floor.

Figure 16:
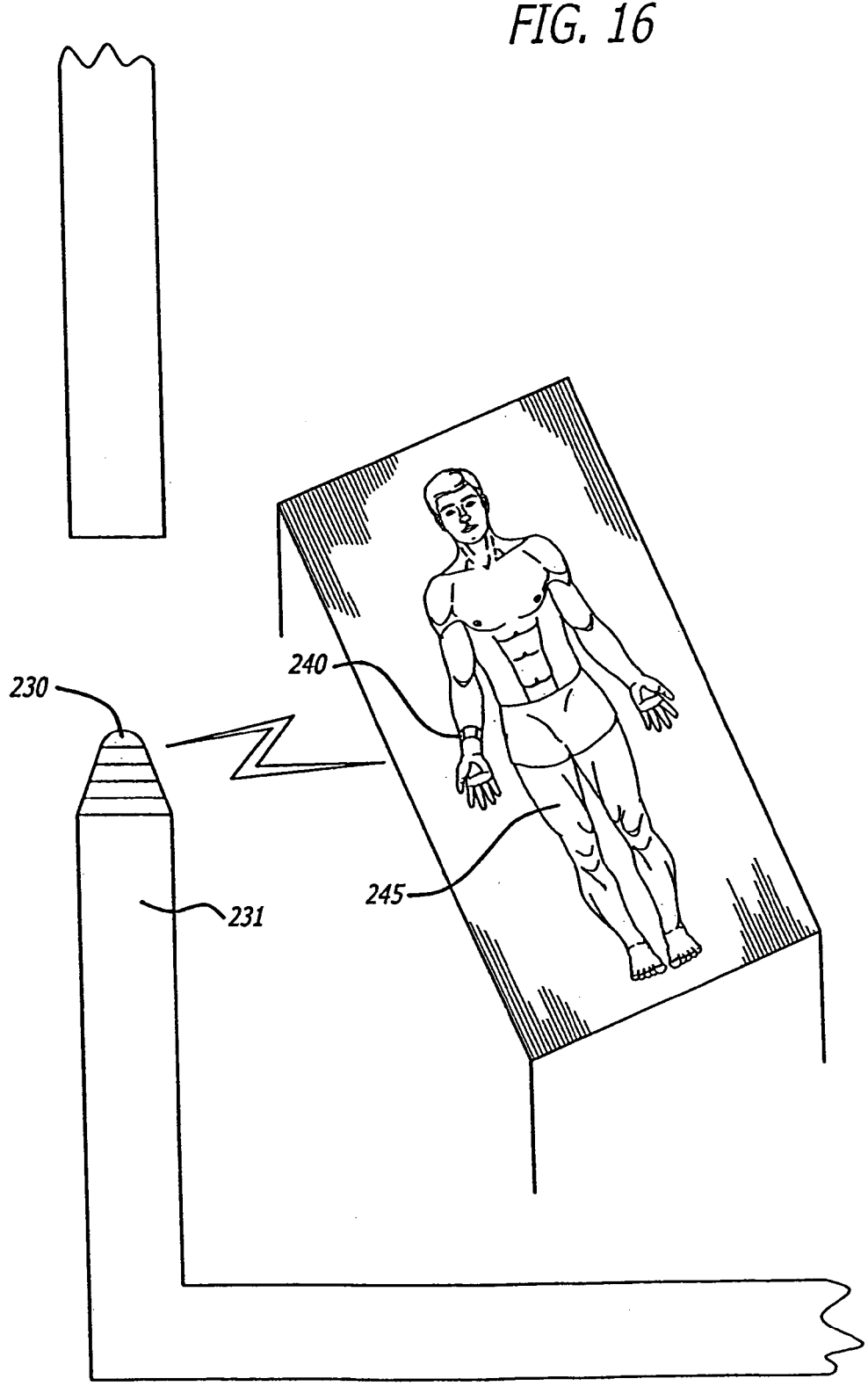
FIG. 16 presents a view of a patient having an identification device located on his arm that interacts with a transmitter/receiver located in the frame of the entry/exit of the room in which the patient is located. The identification device and transmitter/receiver form a passive identification system in accordance with an aspect of the invention.

Another embodiment of the care management system 30 is shown in FIG. 16. In this embodiment, the patient 245 and/or caregiver have badges or wrist bands 240 that may also include electronic circuitry that is responsive to signals from a transmitter/receiver 230 located in each patient room or treatment area to automatically provide the care management system 30 (FIG. 1) with the identity of, and possibly other selected information about, the occupants of the patient room or treatment area, eliminating the need to use a bar-code reader to read the bar-codes on the patient and/or caregiver badges or wrist bands. Such a system may be described as a passive recognition system in that neither the patient nor the caregiver need take any active steps to inform the care management system 30 of their location within the institution.

One example of such a system incorporates an intelligent RF computer chip into the caregiver or patient badge or wristband 240 that provides a unique, or programmed response with a passive RF transponder 230 located within a patient room or treatment area, such as in the frame 231 of the entry or exit of the room or treatment area, or mounted on a wall or ceiling. Each badge or wrist band 240 interacts with signals of the transponder 230 in a unique way, the unique interaction representing an assigned code for the badge or wristband 240. Utilizing this technology would remove manual steps and some of the "human factor" from the process of identifying the patient and caregiver.

When an individual 245 wearing a badge or wristband 240 having such a circuit enters a room or area where a transmitter/receiver 230 is located, the electronic circuit in the badge or wristband 240 interacts with signals emitted by the transmitter without any positive action on the part of the caregiver or the patient. This interaction may be sensed by the receiver, which may be capable of determining the identity of the badge or wristband 240 from the interaction of the electronic circuit with the emitted signals. Alternatively, the receiver may simply sense the interaction and provide a signal representative of the sensed interaction to a computer or other processor which has been programmed or otherwise configured to determine the identity of the individual associated with that particular badge or wristband 240.

Although the preceding paragraphs describe a passive recognition system using electrical circuitry, other approaches may also be used. For example, it can be envisioned that the patient and/or caregiver may have magnetically-encoded devices that can be automatically read by an appropriate detector located in the patient room or treatment area.

Such a system is advantageous in that it can also be used to track the location of patients and caregivers in an institution. This information would be useful to monitor patient movements, especially in the case of patients with reduced mental capacity who may be prone to wandering about the institution. It would also be useful to know the location of the caregivers within an institution so that in the event of an emergency, the caregiver could be quickly located.

While several forms of the invention have been illustrated and described, it will also be apparent that various modifications can be made without departing from the spirit and scope of the invention. Accordingly, it is not intended that the application be limited, except by the appended claims.

The invention claimed is:

1. A system for programming a clinical device to deliver medication to a patient, the system comprising:
    a first processor in operable communication with the clinical device; input means operatively connected to the first processor for input of identification data to the first processor;
    a second processor having a memory in which is stored information related to the delivery of medication to the patient, including identification data;
    a means for communicating information related to the delivery of medication to the patient between the first and second processors, the information including identification data and clinical device operating parameters;

wherein identification data input into the first processor is compared to the stored identification data by either the first or second processor and the second processor downloads clinical device operating parameters to the first processor to program and operate the clinical device in accordance with the downloaded operating parameters if the comparison of the identification data satisfies a predetermined condition.

2. The system of claim 1, wherein the information related to the delivery of medication to the patient stored within the memory further includes clinical device location data, and the communication means is also for communicating the clinical device location data from the first processor to the second processor for storing the clinical device location data in the memory.

3. The system of claim 1, wherein the information related to the delivery of medication to the patient stored in the memory further includes clinical device usage data and the communication means is also for communicating clinical device usage data from the first processor to the second processor for storing the clinical device usage data in the memory.

4. The system of claim 1, wherein the information related to the delivery of medication to the patient stored in the memory further includes clinical device maintenance data and the communication means is also for communicating clinical device maintenance data from the first processor to the second processor for storing the clinical device maintenance data in the memory.

5. The system of claim 1, wherein the information related to the delivery of medication to the patient stored in the memory includes medical administration records, each medical administration record including patient identification data and medical treatment data.

6. The system of claim 5, wherein the medical treatment data includes clinical device operating parameters.

7. The system of claim 5, wherein the communication means is also for communicating medical treatment data input into the first processor by the input means to the second processor for storing the medical treatment data in the medical administration record corresponding to the patient being treated.

8. The system of claim 1, wherein the communication means includes a first transmitter/receiver operatively connected to the first processor for transmitting and receiving information related to the delivery of medication to the patient to and from the second processor; and
a second transmitter/receiver operatively connected to the second processor for transmitting and receiving information related to the delivery of medication to the patient to and from the first processor.

9. The system of claim 1, wherein the first input means comprises a barcode reader.

10. The system of claim 1, wherein the first input means comprises an RF transponder.

11. The system of claim 10, further comprising an identification device located on an individual;
wherein the RF transponder interacts with the identification device to provide a signal to the first processor representing the identity of the individual.

12. The system of claim 11, wherein the identification device comprises an electrical circuit.

13. A system for programming a clinical device to deliver medication to a patient comprising:
a first processor operably connected to the clinical device;
a sensor in communication with the first processor, the sensor including circuit means for transmitting a signal and for receiving information related to the delivery of medication communicated to the sensor in response thereto, wherein the received information is communicated to the first processor;
a passive identification device located on a patient including means responsive to the signal to communicate the information related to the delivery of medication to the sensor;
a second processor having a memory in which is stored information related to the delivery of medication to the patient;
a means for communicating information related to the delivery of medication to the patient between the first and second processors, the information including identification data and clinical device operating parameters;
wherein identification data input into the first processor is compared to the stored identification data by either the first or second processor and the second processor downloads clinical device operating parameters to the first processor to program and operate the clinical device in accordance with the downloaded operating parameters if the comparison of the identification data satisfies a predetermined condition.

14. A method for programming a clinical device to deliver medication to a patient comprising:
storing identification information in a memory;
sensing identification information from an identification device associated with a patient;
comparing the sensed identification information with the stored identification information; and
communicating clinical operating parameters to the clinical device to program the clinical device if the comparison of the sensed identification information with the stored identification information satisfies a predetermined condition.

* * * * *

(12) EX PARTE REEXAMINATION CERTIFICATE (8985th)
United States Patent
Engleson et al.

(10) Number: US 7,117,041 C1
(45) Certificate Issued: *Apr. 24, 2012

(54) SYSTEM AND METHOD FOR PROGRAMMING A CLINICAL DEVICE

(75) Inventors: Joseph J. Engleson, Carlsbad, CA (US); Craig Chamberlain, Ann Arbor, MI (US)

(73) Assignee: Carefusion 303, Inc., San Diego, CA (US)

Reexamination Request:
No. 90/011,051, Jun. 16, 2010

Reexamination Certificate for:
Patent No.: 7,117,041
Issued: Oct. 3, 2006
Appl. No.: 11/024,564
Filed: Dec. 28, 2004

( * ) Notice: This patent is subject to a terminal disclaimer.

Related U.S. Application Data

(63) Continuation of application No. 10/622,983, filed on Jul. 18, 2003, now Pat. No. 6,915,170, which is a continuation of application No. 09/114,581, filed on Jul. 13, 1998, now Pat. No. 6,671,563, which is a continuation-in-part of application No. 08/440,625, filed on May 15, 1995, now Pat. No. 5,781,442.

(51) Int. Cl.
*G05B 19/18* (2006.01)
*G05B 15/02* (2006.01)
*A61B 5/00* (2006.01)
*A61K 9/22* (2006.01)

(52) U.S. Cl. .................. 700/2; 700/9; 600/300; 604/890.1; 705/3

(58) Field of Classification Search .............. None
See application file for complete search history.

(56) References Cited

To view the complete listing of prior art documents cited during the proceeding for Reexamination Control Number 90/011,051, please refer to the USPTO's public Patent Application Information Retrieval (PAIR) system under the Display References tab.

*Primary Examiner* — Zoila Cabrera

(57) ABSTRACT

A care management system in which the management of the administration of care for patients is automated. Hospital information systems are monitored and the information from those systems is used in verifying the administrations of care to patients. The care management system monitors ongoing administrations for progress and automatically updates records and provides alarms when necessary. The care management system is modular in nature but is fully integrated among its modules. Particular lists of data, such as the termination times of all ongoing infusions, provide hospital staff current information for increased accuracy and efficiency in planning. Features include the automatic provision of infusion parameters to pumps for accurate and efficient configuration of the pump, and providing an alarm when an unscheduled suspension of an infusion exceeds a predetermined length of time. A passive recognition system for identifying patients and care givers is provided.

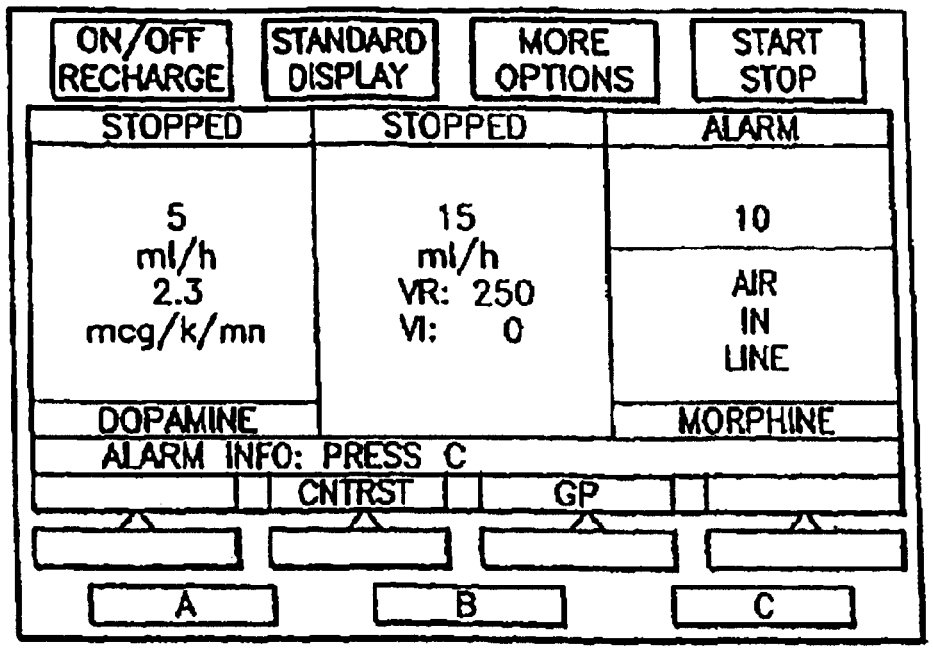

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-13 is confirmed.

Claim 14 is determined to be patentable as amended.

14. A method for programming a clinical device to deliver medication to a patient comprising:

storing identification information in a memory;

sensing identification information from an identification device associated with a patient;

comparing the sensed identification information with the stored identification information; and communicating clinical operating parameters *from a pharmacy computer through a communication network* to the clinical device to program the clinical device if the comparison of the sensed identification information with the stored identification information satisfies a predetermined condition.

\* \* \* \* \*